United States Patent
Haga et al.

(10) Patent No.: US 9,018,125 B2
(45) Date of Patent: Apr. 28, 2015

(54) DIETHYLZINC COMPOSITION, METHOD FOR HEAT STABILIZATION, AND COMPOUND FOR HEAT STABILIZATION

(71) Applicant: Tosoh Finechem Corporation, Yamaguchi (JP)

(72) Inventors: Kenichi Haga, Yamaguchi (JP); Shizuo Tomiyasu, Yamaguchi (JP); Kohichi Tokudome, Yamaguchi (JP)

(73) Assignee: Tosoh Finechem Corporation, Yamaguchi (JP)

( * ) Notice: Subject to any disclaimer, the term of this patent is extended or adjusted under 35 U.S.C. 154(b) by 0 days.

(21) Appl. No.: 14/231,125

(22) Filed: Mar. 31, 2014

(65) Prior Publication Data

US 2014/0228207 A1     Aug. 14, 2014

Related U.S. Application Data

(62) Division of application No. 13/394,129, filed as application No. PCT/JP2010/005379 on Sep. 1, 2010, now Pat. No. 8,722,561.

(30) Foreign Application Priority Data

| Sep. 2, 2009 | (JP) | 2009-202294 |
| Jan. 5, 2010 | (JP) | 2010-006483 |
| Feb. 1, 2010 | (JP) | 2010-019853 |

(51) Int. Cl.
  *C07F 3/06* (2006.01)
  *C08F 4/50* (2006.01)

(52) U.S. Cl.
  CPC ... *C07F 3/06* (2013.01); *C08F 4/50* (2013.01); *C08F 2410/01* (2013.01)

(58) Field of Classification Search
  None
  See application file for complete search history.

(56) References Cited

U.S. PATENT DOCUMENTS

| 3,394,118 A | 7/1968 | Boor |
| 3,400,082 A | 9/1968 | Gluckstein et al. |
| 2011/0028654 A1 | 2/2011 | Sita et al. |

FOREIGN PATENT DOCUMENTS

| JP | 60-237091 A | 11/1985 |
| JP | 2007-100077 A | 4/2007 |
| JP | 2008-7766 A | 1/2008 |

OTHER PUBLICATIONS

Matsubara et al., "Cyclopropanation of alkenes with CH2I2/Et3Al by the phase-vanishing method based on fluorous phase screen", Journal of Fluorine Chemistry, 2008, 129(10), p. 951-954 (p. 952, tables 1,2).
Yasuo Kuniya et al., "Physicochemical Properties of Dimethylzinc, Dimethylcadmium and Diethylzinc", Applied Organometallic Chemistry, vol. 5, pp. 337-347, Apr. 1991.
Yuki Kagaku, "Seikagaku Meimeiho First volume," Nankodo Co., Ltd. May 20, 1992, 2nd edition, 2nd print, pp. 20 to 21, 40.

*Primary Examiner* — Yun Qian
(74) *Attorney, Agent, or Firm* — Arent Fox LLP

(57) ABSTRACT

[Object]
To improve heat stability of diethylzinc which is used for a catalyst of polymerizing, an organic synthetic reaction reagent and a raw materials for providing a zinc film by MOCVD. And to offer the diethylzinc composition being superior in heat stability, even if it handles for a long term a metal zinc particle does not precipitate.
[Solving Means]
Use a diethylzinc composition added a compound which is added an aromatic compound as an additive which has isopropenyl group bonded as a side chain.

2 Claims, No Drawings

DIETHYLZINC COMPOSITION, METHOD FOR HEAT STABILIZATION, AND COMPOUND FOR HEAT STABILIZATION

CROSS-REFERENCE TO RELATED APPLICATIONS

This Application is a Divisional of U.S. patent application Ser. No. 13/394,129, filed Mar. 2, 2012; which is a National Phase Entry of International Patent Application No. PCT/JP2010/005379, filed Sep. 1, 2012; which claims priority of Japanese Patent Application Nos. 2010-019853, filed Feb. 1, 2012; 2010-006483, filed Jan. 5, 2010; and 2009-202294, filed Sep. 2, 2009. The disclosures of the prior applications are hereby incorporated in their entirety by reference.

TECHNICAL FIELD

This invention relates to a diethylzinc composition superior in heat stability, a heat stabilization method and a compound for heat stabilization.

BACKGROUND ART

Diethylzinc is known as an extremely useful industrial material, for example as a catalyst for polymerizing a polyethylene oxide and a polypropylene oxide, an organic synthetic reaction reagent when manufacturing intermediates such as medicine or functional materials.

Also recently, as a method to form a zinc oxide film, a technique referred to as the MOCVD (Metal Organic Chemical Vapor Deposition) method is examined. In this method of approach, diethylzinc is used as a raw material and steam is used as an oxidizer.

A zinc oxide film provided by the MOCVD method has wide applications, that is, the zinc oxide film is used as a buffer layer of a CIGS solar battery, a transparent conductive film, an electrode membrane of a dye sensitization solar battery, a middle layer of a thin film Si solar battery, various function films in a solar battery such as a transparent conductive film, a photocatalyst film, a film intercepting ultraviolet rays, a film reflecting infrared rays, various function films such as antistatic films, a compound semiconductor light emitting element and electronic devices such as thin-film transistors.

It is known (e.g., non-patent document 1) that the diethylzinc gradually resolves by adding heat and precipitates zinc metal particles. Therefore, in the handling of the diethylzinc, there are problems of a fall off in product purity, pollution of a storage container and constriction of a production facility pipe. These are caused by the deposition of zinc metal particles formed by thermolysis.

As a method to solve the problems due to the deposition of the zinc metal precipitated by the above described thermolysis, a method is known which stabilizes the diethylzinc composition by adding compounds such as anthracene, acenaphthene, acenaphthylene (e.g., patent document (1)-(3)).

PRIOR ART

Patented Documents

[Patent Document 1] U.S. Pat. No. 4,385,003
[Patent Document 2] U.S. Pat. No. 4,402,880
[Patent Document 3] U.S. Pat. No. 4,407,758

Non-Patent Document

[Non Patent Document 1] Yasuo Kuniya et Al. Applied Organometallic Chemistry, 5 vol. 337-347 pages, published 1991

DISCLOSURE OF THE INVENTION

Object of the Invention

As disclosed in Patent Document 1-3, even the addition of anthracene, acenaphthene or acenaphthylene cannot stabilize diethylzinc sufficiently. Therefore a diethylzinc which is superior in heat stability is required.

And anthracene, acenaphthene or acenaphthylene is solid compound at room temperature, there is a problem that an operation such as powder injection is required in the preparation of the diethylzinc composition.

As described above, anthracene, acenaphthene or acenaphthylene is solid compound at room temperature about 25 degrees Celsius, an operation such as powder injection is required in the preparation of the diethylzinc composition. Generally, the vapor pressure of a material with a high melting point is low, when diethylzinc is used in CVD film formation, performing a bubbling of the carrier gas, diethylzinc is supplied as a saturated gas in the carrier gas, in this case, anthracene, acenaphthene or acenaphthylene might remain without vaporizing.

In addition, when a diethylzinc composition is produced using those solid compounds as additives, the additives are fed into the diethylzinc using solid injection machines, and, if the additives become clogged, action is necessary to avoid the diethylzinc being polluted by impurities.

To remove the clogged additives, it is effective to heat the additives and melt them. To this end it is preferable that the additives are compounds with a low melting point.

The purpose of the first invention is to supply a diethylzinc composition which improves the heat stability of the diethylzinc which is used as a catalyst for polymerizing, as an organic synthetic reaction reagent or as a raw material for producing materials such as zinc oxide films by the MOCVD method. For this purpose, aromatic compounds which have isopropenyl group bonded as a side chain are used as an additive.

The purpose of the second invention is to supply a diethylzinc composition and a heat stabilization method which improves the heat stability of the diethylzinc which is used as a catalyst for polymerizing, as an organic synthetic reaction reagent or as a raw material for producing materials such as zinc oxide films by the MOCVD method.

For this purpose easy to handle compounds such as liquids at 25 degrees Celsius, that is a compound of which melting or freezing point is less than 25 degrees Celsius, is used as an additive.

The purpose of the third invention is to supply a diethylzinc composition and a heat stabilization method which improves the heat stability of the diethylzinc which is used as a catalyst for polymerizing, as an organic synthetic reaction reagent or as a raw material for producing materials such as zinc oxide films by the MOCVD method and also to reduce the problem of residual additive.

For this purpose a compound which has a lower melting point than the well-known (commonly used) additive, that is a compound which has a melting or freezing point below 85 degrees Celsius, is used as an additive.

The purpose of the fourth invention is to improve the heat stability of the diethylzinc which is used as a catalyst for polymerizing, as an organic synthetic reaction reagent or as a raw material for producing materials such as zinc oxide films by the MOCVD method. For this purpose a compound which has an azulene structure is used as an additive.

Means for Solving the Problem

In order to solve the above mentioned problems, the inventors of the present invention researched and developed zealously. As a result, the inventors found that the heat stability of diethylzinc (CAS No. 557-20-0) improved remarkably by coexisting an aromatic compound which has an isopropenyl group bonded as a side chain. Then the inventors completed the first invention.

To a diethylzinc composition of the first invention is added an aromatic compound as an additive which has an isopropenyl group bonded as a side chain.

And a diethylzinc composition of the first invention includes one or more aromatic compounds which have an isopropenyl group bonded as a side chain represented by the following formula (1), (2) and (3).

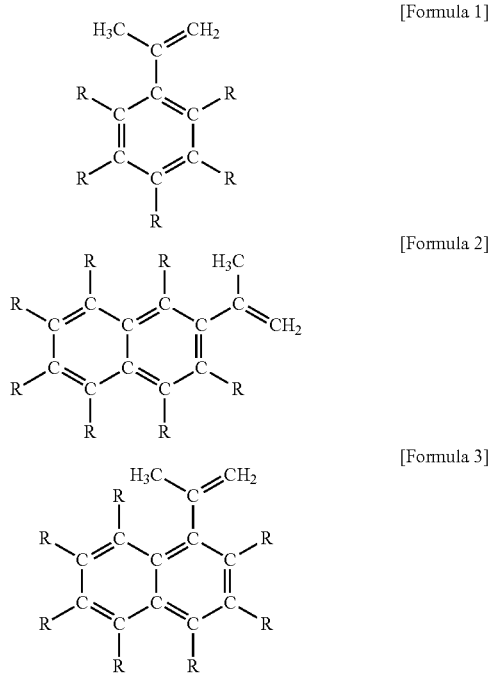

[Formula 1]

[Formula 2]

[Formula 3]

In the formula (1), (2) and (3), R represents respectively, hydrogen, a straight chain or branched alkyl group which has 1-8 carbon atoms, a straight chain or branched alkenyl group (including an isopropenyl group) which has 1-8 carbon atoms and an allyl group which has 6-14 carbon atoms.

A substituent group R bonded as a side chain of aromatic compound which is represented by the formula (1), (2) and (3) is not only isopropenyl group but also a hydrogen, a straight chain or branched alkyl group which has 1-8 carbon atoms such as a methyl or isopropyl group, a straight chain or branched alkenyl group which has 1-8 carbon atoms such as a vinyl or propenyl group (including isopropenyl as described before), and an allyl group which has 6-14 carbon atoms such as a phenyl or toluyl group.

There may be a plural number of isopropenyl bonded as a side chain, in the case of benzene having two isopropenyl as aromatic compounds, 1,3-diisopropenyl benzene and 1,4-diisopropenyl benzene are superior in heat stability.

As the aromatic compounds which have isopropenyl group bonded as a side chain, α-methyl styrene, 4-isopropenyl toluene, 1-isopropenyl naphthalene, 2-isopropenyl naphthalene as one substitute of isopropenyl, 1,3-diisopropenyl benzene, 1,4-diisopropenyl benzene, 1,3,5-triisopropenyl benzene, 2,4-diisopropenyl naphthalene as more than two substitutes of isopropenyl are exemplified.

Of these aromatic compounds, α-methyl styrene, 4-isopropenyl toluene, 1,3-diisopropenyl benzene, 1,4-diisopropenyl benzene, 2-isopropenyl naphthalene are preferable because their structure is simple, they are easily acquired industrially and a good result can be expected.

In particular, α-methyl styrene, 4-isopropenyl toluene, 1,3-diisopropenyl benzene, are liquid at a temperature of about 20 degrees Celsius, then a preparation of diethylzinc composition can be performed easily.

ARC measurement (Accelerating Rate calorimetry) is generally used to examine heat stability as its acceleration test and, from the results of the ARC measurement, a diethylzinc composition of the first invention has superior heat stability at temperatures below 180 degrees Celsius. Since the results of the ARC test measurements have temperature dependency, as the temperature falls, the effect of the diethylzinc composition on the heat stability is performed well.

And in order to solve the above mentioned problems, the inventors of the present invention researched and developed zealously. As a result, the inventors found that the heat stability of diethylzinc (CAS No. 557-20-0) improved remarkably by coexisting the following 1)~4) compound as an additive, the melting point or the freezing point of the additive is 25 degrees Celsius or less, 1) particular aromatic compounds having isopropyl group bonded as a side chain, 2) particular compound having fulvene structure, 3) squalene, 4) 2,4-diphenyl-4-methyl-1-pentene. Then the inventors completed the second invention.

A diethylzinc composition of the second invention has a compound added as an additive which has a melting point of 25 degrees Celsius or less, that is liquid at 25 degrees Celsius, specifically to a diethylzinc composition is added one or more compounds of 1) particular aromatic compounds having isopropyl group bonded as a side chain, 2) particular compound having fulvene structure, 3) squalene, 4) 2,4-diphenyl-4-methyl-1-pentene.

And as 1) particular aromatic compounds having isopropyl group bonded as a side chain of the diethylzinc composition of the second invention, includes one or more compounds represented by the following formula (4), (5), (6), (7) and (8).

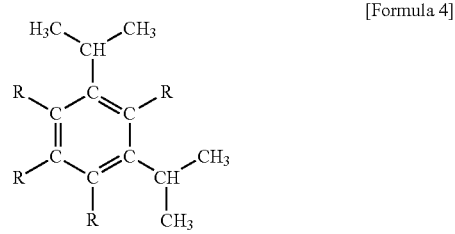

[Formula 4]

-continued

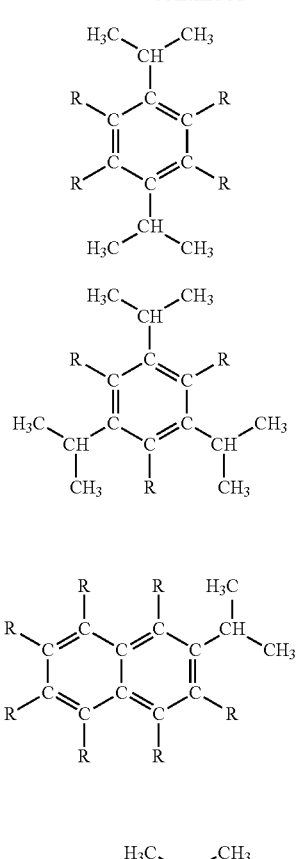

[Formula 5]

[Formula 6]

[Formula 7]

[Formula 8]

In the formula (4), (5), (6), (7) and (8), R represents respectively, hydrogen, a straight chain or branched alkyl group (including isopropyl group) which has 1-8 carbon atoms, a straight chain or branched alkenyl group which has 1-8 carbon atoms, an allyl group which has 6-14 carbon atoms.

A substituent group R bonding as a side chain of aromatic compound which is represented by the formula (4), (5), (6), (7) and (8) is not only an isopropyl group but also a hydrogen, a straight chain or branched alkyl group (including isopropyl group) which has 1-8 carbon atoms such as a methyl or isopropyl group, a straight chain or branched alkenyl group which has 1-8 carbon atoms such as vinyl or propenyl group, and allyl group which has 6-14 carbon atoms such as a phenyl or toluyl group. The number of isopropyl bonding as a side chain may be a plural, in the case of benzene having two isopropyls as aromatic compounds, 1,3-diisopropyl benzene, 1, 4-diisopropyl benzene and 1,3,5-triisopropyl benzene are superior in heat stability.

As the aromatic compounds which have isopropyl group bonded as a side chain, 1-isopropyl naphthalene, 2-isopropyl naphthalene as one substitute of isopropyl, 1,3-diisopropyl benzene, 1,4-diisopropyl benzene, 1,3,5-triisopropyl benzene as more than two substitutes of isopropyl are exemplified.

Among these aromatic compounds, 1-isopropyl naphthalene, 2-isopropyl naphthalene 1,3-diisopropyl benzene, 1,4-diisopropyl benzene and 1,3,5-triisopropyl benzene are preferable, because their structure is simple, they can be easily acquired industrially and good results can be expected.

These aromatic compounds which have isopropyl group bonded as a side chain are liquid at 25 degrees Celsius, thus a preparation of diethylzinc composition can be performed easily.

And as 2) particular compound having fulvene structure of the second invention are exemplified by the following formula (9).

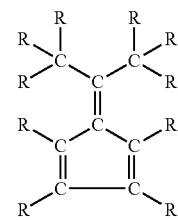

[Formula 9]

In the formula (9), R represents respectively, hydrogen, a straight chain or branched alkyl group which has 1-8 carbon atoms, a straight chain or branched alkenyl group which has 1-8 carbon atoms, an allyl group which has 6-14 carbon atoms.

Among these particular compounds having fulvene structure, 6,6-dimethyl fulvene (CAS No. 2175-91-9) is preferable, because the structure is simple, industrial acquisition is easy and good results can be expected.

The particular compound having fulvene structure is liquid at 25 degrees Celsius, thus a preparation of diethylzinc composition can be performed easily.

Said 3) squalene (CAS No.111-02-4) and 4) 2,4-diphenyl-4-methyl-1-pentene (CAS No. 6362-80-7) of the second invention can be used as a diethylzinc composition.

And in order to solve the above mentioned problems, the inventors of the present invention researched and developed zealously. As a result, the inventors found that the heat stability of diethylzinc (CAS No. 557-20-0) improved remarkably by coexisting naphthalene compound as an additive, the melting point or freezing point of the naphthalene compound is 85 degrees Celsius or less. Then the inventors completed the third invention.

A diethylzinc composition of the third invention has a naphthalene compound added as an additive of which melting or freezing point is 85 degrees Celsius or less.

And the naphthalene compound includes one or more than two compounds selected from the following formula (1), (2) and (3).

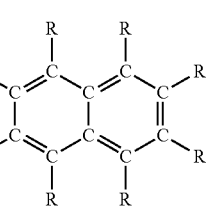

[Formula 10]

-continued

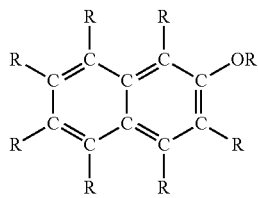
[Formula 11]

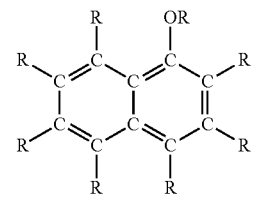
[Formula 12]

In the formula (10), (11) and (12), R represents respectively, hydrogen, a straight chain or branched alkyl group (including isopropyl group) which has 1-8 carbon atoms, a straight chain or branched alkenyl group which has 1-8 carbon atoms, an allyl group which has 6-14 carbon atoms.

As the naphthalene compound of which melting or freezing point is 85 degrees Celsius or less, naphthalene is exemplified, also, 2-methylnaphthalene, 2,6-diisopropyl naphthalene are exemplified as a compound which has an alkyl group bonded as a side chain, 1-styryl naphthalene is exemplified as a compound which has an alkenyl group or allyl group, 2-methoxynaphthalene is exemplified as a compound of said formula (3).

Among these aromatic compounds, naphthalene, 2-methylnaphthalene, 2,6-diisopropyl naphthalene, 1-styryl naphthalene and 2-methoxynaphthalene are preferable, because the structure is simple, they are easily acquired industrially and good results can be expected. The melting point of these naphthalene compounds is 85 degrees Celsius or less.

A diethylzinc composition of the fourth invention has a compound added as an additive which has an azulene structure. The azulene structure is widely known, that is, as shown in following formula (13), a ring structure comprised of 7 carbon atoms and a ring structure comprised of 5 carbon atoms are connected.

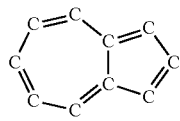
[Formula 13]

And a diethylzinc composition of the fourth invention includes a compound which has an azulene structure represented following the formula (14).

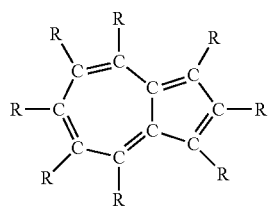
[Formula 14]

In the formula (14), R represents respectively, hydrogen, a straight chain or branched alkyl group which has 1-8 carbon atoms, a straight chain or branched alkenyl group which has 1-8 carbon atoms, an allyl group which has 6-14 carbon atoms.

A substituent group R is bonded as a side chain of a compound which has an azulene structure, as the substituent group R, hydrogen, a straight chain or branched alkyl group which has 1-8 carbon atoms such as a methyl group or an isopropyl group, a straight chain or branched alkenyl group which has 1-8 carbon atoms (including isopropenyl as described before) such as a vinyl, propenyl or isopropenyl, and allyl group which has 6-14 carbon atoms such as phenyl group or toluyl group. The number of substituent groups bonding as a side chain may be different, it may be a single number or a plural number of two or more.

Various substituted azulene compounds such as azulene, guaiazulene and lactarazulene are exemplified as the compounds which have an azulene structure.

Among these compounds which have an azulene structure, azulene (CAS No. 275-51-4), guaiazulene(CAS No. 489-84-9) and lactarazulene (CAS No. 489-85-0) are preferable, because their structure is simple, they are easily acquired industrially and good results can be expected.

As for the additive as used herein, sufficient effects are provided by independent addition, and a plural number of them may be mixed together.

Herein, concerning to the quantity of addition of the compound of the first~fourth invention, there is no specific limitation on the quantity added as long as the performance of diethylzinc is maintained and a heat stabilization effect is provided. Usually, when the ratio to diethylzinc is 100 ppm-20 wt %, preferably 200 ppm-1.0 wt %, more preferably 500 ppm-5 wt %, a diethylzinc composition superior in heat stability can be obtained.

If the quantity of the added compound of the present invention is too small then sufficient heat stability improvement effects may not be provided, and if the quantity of the compound added is too much an effect to balance with quantity of addition is not provided. Therefore, it is desirable to add an appropriate amount to obtain a desired effect with reference to heat stability.

As for the diethylzinc to be use for carrying out the present invention, diethylzinc generally known as an industrial material can be chosen, such as a polymerization catalyst of polyethylene oxide or polypropylene oxide, a reaction reagent for synthesizing an intermediate of medicine or functional materials.

Also, in the present invention, diethylzinc of a higher purity than that of the industrial material can also be used.

This high purity diethylzinc is used to form a zinc oxide film by the MOCVD method. The zinc oxide film is applied as a buffer layer of a CIGS solar battery, a transparent conductive film, an electrode film of a dye sensitization solar battery, a middle layer of a film Si solar battery, various functional films of a solar battery, a photocatalyst film, an ultraviolet ray interception film, an infrared reflection film, various functional films such as antistatic films, a compound semiconductor light emitting element, and electronic devices such as thin-film transistors.

To prepare the diethylzinc composition of the present invention, there is no specific limitation on how to mix them, the additive compound of the first~third invention can merely be added to the diethylzinc.

For example, to attempt the improvement of the stability in storage, the additive to the diethylzinc can be added beforehand. Also, for example, when the diethylzinc composition is used for a reaction, the additive to the diethylzinc may be added just before use.

And as for the temperature of the preparation of the diethylzinc composition of the present invention, 70 degrees Celsius or less is desirable since a thermolysis of the diethylzinc does not proceed fast. Usually, the preparation of the composition of the present invention can be performed at −20~35 degrees Celsius. About the pressure, there is no particular limit either, usually the diethylzinc and the composition of the present invention can be prepared at around atmospheric pressure such as 0.1013 MPa except in a special case such as reaction.

Concerning the machine parts and the atmosphere for using a storage container, a transportation container, a storage tank and a facility such as the pipe for the diethylzinc composition of the present invention, the facilities and atmosphere used for diethylzinc can simply be converted.

For example, SUS, carbon steel, titanium, a metal such as Hastelloy, teflon (registered trademark) and resin such as a fluorine-based rubber are applicable as materials of the above mentioned machine parts.

Also, regarding the atmosphere, inert gases such as nitrogen, helium, argon—as in the case of the diethylzinc can be used.

And the diethylzinc composition of the present invention can dissolve in a well-known solvent which can be used for dissolving the diethylzinc. The following are examples of the solvent. A saturated hydrocarbon such as pentane, hexane, heptane and octane, an aromatic hydrocarbon such as benzene, toluene and xylene, an ether-based compounds such as a diethyl ether, isopropyl ether, tetrahydrofuran, dioxane or diglyme.

As for the application of the diethylzinc composition of the present invention, it is similar to the application of the diethylzinc as used conventionally. That is, for example, a polymerization catalyst of polyethylene oxide or polypropylene oxide, a reaction reagent of synthesizing an intermediate of medicine or functional materials. Also, the diethylzinc composition of the present invention can be applied to form a zinc oxide film by the MOCVD method. The zinc oxide film is applied as a buffer layer of a CIGS solar battery, a transparent conductive film, an electrode film of a dye sensitization solar battery, a middle layer of a film Si solar battery, various functional films of the solar battery, a photocatalyst film, an ultraviolet ray interception film, an infrared reflection film, various functional films such as antistatic films, a compound semiconductor light emitting element, application for forming an oxide used in an electronic devices such as thin-film transistor, application for forming a film of an electronic devices of II-VI group such as ZnS.

Effect of the Invention

The diethylzinc composition added the additive of the present invention is superior in heat stability, and the deposition of zinc metal particles is extremely small, thus it can prevent a fall off in product purity, pollution of the storage container and plugging of the production facility pipe.

BEST MODE FOR CARRYING OUT THE INVENTION

The present invention is explained below in detail with embodiments, these embodiments do not limit the present invention.

Measuring Equipment

DSC measurement was carried out using a DSC6210 (made by SEIKO Instruments Co., Ltd.)

ARC measurement was carried out using an ARC2000 (made by ADL Co., Ltd. (Authur D Little))

Preparation of the Diethyl Zinc Composition

Diethylzinc (made by TOSOH FINECHEM Corporation) and additives (commercial reagent) comprising various kinds of the aromatic compounds which have an isopropenyl group as a side chain were weighted in a glass container by predetermined density under a nitrogen atmosphere at room temperature. A diethylzinc composition was then prepared by dissolving the additive into the diethylzinc.

The addition rate of the additive to diethylzinc (weight percent) is calculated using the following formula.

Addition rate (weight percent) of the additive=(additive weight/(additive weight+diethylzinc weight))×100

For the diethylzinc composition prepared by the above-mentioned method, the heat stabilization effect of the additive was evaluated by carrying out DSC measurement (Differential Scanning calorimetry), ARC measurement (Accelerating Rate calorimetry) and a long-term heat stability examination. It shows that the heat stabilization effect of the additive on diethylzinc is high so that the initial, exothermic temperature of measurement is high.

REFERENCE 1

Heat Stabilization Examination by DSC Measurement of Diethylzinc

Under a nitrogen atmosphere, weighted the diethylzinc and sealed in a DSC cell made of SUS. Carried out a thermal analysis on the provided sample by the DSC method, the measurement temperature range was 30-450 degrees Celsius, and the rate of temperature increase was 10 degrees Celsius/minute. The resolution temperature of each sample is observed at the initial exothermic temperature of DSC measurement. The initial exothermic temperature of the sample of diethylzinc which did not have an additive is shown in Table 1.

EXAMPLE 1-5

Heat Stabilization Examination by DSC Measurement to Diethylzinc Composition

Similarly to Reference 1, under a nitrogen atmosphere, weighted the diethylzinc composition added various kinds of the aromatic compounds having an isopropenyl group as a side chain which is a compound of the present invention, and sealed in a DSC cell made of SUS. Similarly to Reference 1, carried out a thermal analysis to the provided samples by DSC method, the measurement temperature range was 30-450 degrees Celsius, and the rate of temperature increase was 10 degrees Celsius/minute. The initial exothermic temperatures of the samples of diethylzinc composition are shown in Table 1.

The initial exothermic temperature of the sample of the diethylzinc composition to which were added various kinds of the aromatic compounds having an isopropenyl group as a side chain of the present invention is higher than the initial exothermic temperature of the sample of diethylzinc only provided by the reference, and the start temperature of the resolution of the composition of the present invention is higher than the start temperature of the sample of diethylzinc only. From this result it is confirmed that the diethylzinc composition to which was added to an additive has a superior heat stability.

COMPARATIVE EXAMPLE 1-2

As a diethylzinc composition to which is not added various kinds of the aromatic compounds having an isopropenyl group as a side chain, prepare benzene and toluene which replaced the isopropenyl of the compound in example 1-5 with hydrogen. and similarly to Example 1-5, carried out the examination to the diethylzinc composition which added benzene and toluene. The initial exothermic temperatures of the samples are shown in Table 1.

From the result of comparative example 1-2, it is confirmed that the samples are inferior to a composition of the present invention in heat stability, and from this result it is confirmed that if an isopropenyl (group) is bonded as a side chain it has a large effect on heat stability.

COMPARATIVE EXAMPLE 3-5

Similarly to Example 1-5, carried out the examination of the diethylzinc composition to which was added anthracene, acenaphthene and acenaphthylene, these are the compounds as described in Patent Document 1-3. The initial exothermic temperatures of the samples are shown in Table 1.

The initial exothermic temperature of these samples are lower than the initial exothermic temperature of the sample to which was added various kinds of the aromatic compounds having an isopropenyl group as a side chain which is a compound of the present invention. From this result, it is confirmed that the composition to which was added an existing/conventional additive is inferior to a composition of the present invention in heat stability.

TABLE 1

| Example | Diethylzinc composition | Additive | Ratio of the additive (%) | DSC sample quantity (mg) | DSC initial exothermic temperature (° C.) |
| --- | --- | --- | --- | --- | --- |
| Reference 1 | Diethylzinc | None | 0 | 2.7 | 182.9 |
| Example 1 | Diethylzinc-α-Methylstyrene | α-Methylstyrene | 4.47 | 3.0 | 204.2 |
| Example 2 | Diethylzinc-4-Isopropenyltoluene | 4-Isopropenyltoluene | 4.69 | 3.0 | 202.2 |
| Example 3 | Diethylzinc-1,3-Diisopropenylbenzen | 1,3-Diisopropenylbenzen | 4.57 | 3.0 | 206.0 |
| Example 4 | Diethylzinc-1,4-Diisopropenylbenzen | 1,4-Diisopropenylbenzen | 4.34 | 3.4 | 207.1 |
| Example 5 | Diethylzinc-1,2-Isopropenylnaphthalene | 1,2-Isopropenylnaphthalene | 4.41 | 1.7 | 208.9 |
| Comparative Example 1 | Diethylzinc-Benzene | Benzene | 3.96 | 2.8 | 177.0 |
| Comparative Example 2 | Diethylzinc-Toluene | Toluene | 3.77 | 2.9 | 178.7 |
| Comparative Example 3 | Diethylzinc-Anthracene | Anthracene | 4.36 | 3.3 | 188.7 |
| Comparative Example 4 | Diethylzinc-Acenaphthylene | Acenaphthylene | 4.43 | 3.4 | 173.5 |
| Comparative Example 5 | Diethylzinc-Acenaphthene | Acenaphthene | 4.27 | 1.8 | 201.9 |

COMPARATIVE EXAMPLE 6-11

Similarly to Example 1-5, carried out the examination of thermal analysis to the diethylzinc composition to which was added anthracene, acenaphthene and acenaphthylene changing the addition rate, these are the compounds as described in Patent Document 1-3. The initial exothermic temperatures of the samples are shown in Table 2.

TABLE 2

| Example | Diethylzinc composition | Additive | Ratio of the additive (%) | DSC sample quantity (mg) | DSC initial exothermic temperature (° C.) |
| --- | --- | --- | --- | --- | --- |
| Reference 1 | Diethylzinc | None | 0 | 2.7 | 182.9 |
| Comparative Example 6 | Diethylzinc-Anthracene | Anthracene | 0.48 | 2.7 | 187.0 |
| Comparative Example 7 | Diethylzinc-Acenaphthylene | Acenaphthylene | 0.49 | 2.8 | 171.9 |
| Comparative Example 8 | Diethylzinc-Acenaphthene | Acenaphthene | 0.50 | 2.7 | 175.9 |
| Comparative Example 9 | Diethylzinc-Anthracene | Anthracene | 1.05 | 2.9 | 187.5 |
| Comparative Example 10 | Diethylzinc-Acenaphthene | Acenaphthene | 1.00 | 2.9 | 179.8 |
| Comparative Example 11 | Diethylzinc-Acenaphthene | Acenaphthene | 1.05 | 2.9 | 186.1 |

EXAMPLE 6-20

Similarly to Example 1-5, carried out the same examination to the diethylzinc composition changing the addition rate of the additives. The initial exothermic temperatures of the samples are shown in Table 3.

Even if the addition rate of the additives is lowered, the initial exothermic temperature of the sample of the diethylzinc composition to which was added a compound of the present invention is higher than the initial exothermic temperature of the sample of diethylzinc only provided by the reference, also the start temperature of the resolution of the sample of the present invention is higher than the sample of diethylzinc only.

From the results of example 6-19, it is clearly demonstrated that the diethylzinc composition to which was added an additive of the present invention has a superior heat stability.

And the initial exothermic temperature of the sample which is a diethylzinc composition to which was added a group including oxygen, such as the methoxy group, as a side chain R of aromatic compounds is higher than the initial exothermic temperature of the sample of diethylzinc only, and the start temperature of the resolution of the composition of the present invention is higher than the start temperature of the sample of diethylzinc only.

From the result of example 20, it is clearly demonstrated that the diethylzinc composition to which was added a group including oxygen such as the methoxy group as side chain R of aromatic compounds is superior in heat stability.

TABLE 3

| Example | Diethylzinc composition | Additive | Ratio of the additive (%) | DSC sample quantity (mg) | DSC initial exothermic temperature (° C.) |
| --- | --- | --- | --- | --- | --- |
| Example 6 | Diethylzinc-2-Isopropenylnaphthalene | 2-Isopropenylnaphthalene | 8.92 | 3.0 | 209.3 |
| Example 7 | Diethylzinc-2-Isopropenylnaphthalene | 2-Isopropenylnaphthalene | 1.06 | 3.0 | 203.9 |
| Example 8 | Diethylzinc-2-Isopropenylnaphthalene | 2-Isopropenylnaphthalene | 0.43 | 2.9 | 201.4 |
| Example 9 | Diethylzinc-α-Methylstyrene | α-Methylstyrene | 8.95 | 3.3 | 201.0 |
| Example 10 | Diethylzinc-α-Methylstyrene | α-Methylstyrene | 1.06 | 3.2 | 194.6 |
| Example 11 | Diethylzinc-α-Methylstyrene | α-Methylstyrene | 0.43 | 3.2 | 192.2 |
| Example 12 | Diethylzinc-1,3-Diisopropenylbenzen | 1,3-Diisopropenylbenzen | 9.04 | 3.2 | 202.7 |
| Example 13 | Diethylzinc-1,3-Diisopropenylbenzen | 1,3-Diisopropenylbenzen | 1.02 | 3.0 | 204.0 |
| Example 14 | Diethylzinc-1,3-Diisopropenylbenzen | 1,3-Diisopropenylbenzen | 0.47 | 3.2 | 203.1 |
| Example 15 | Diethylzinc-1,3-Diisopropenylbenzen | 1,3-Diisopropenylbenzen | 0.09 | 3.2 | 190.8 |
| Example 16 | Diethylzinc-1,4-Diisopropenylbenzen | 1,4-Diisopropenylbenzen | 19.64 | 2.6 | 214.9 |
| Example 17 | Diethylzinc-1,4-Diisopropenylbenzen | 1,4-Diisopropenylbenzen | 9.02 | 2.7 | 213.2 |
| Example 18 | Diethylzinc-1,4-Diisopropenylbenzen | 1,4-Diisopropenylbenzen | 1.02 | 2.9 | 202.1 |
| Example 19 | Diethylzinc-1,4-Diisopropenylbenzen | 1,4-Diisopropenylbenzen | 0.0204 | 2.8 | 187.9 |
| Example 20 | Diethylzinc-6-Methoxy-2-(1-Methylvinyl) Naphthalene | 6-Methoxy-2-(1-Methylvinyl) Naphthalene | 3.78 | 2.9 | 206.5 |

REFERENCE 2

Heat Stabilization Examination by ARC Measurement to Diethylzinc

Under a nitrogen atmosphere, weighted the diethylzinc and sealed in an ARC cylinder made of hastelloy C. Carried out a thermal analysis on the provided sample by the ARC method, the temperature at the start of the measurement was 50 degrees Celsius, the temperature at the end of the measurement was 350 degrees Celsius, the temperature was raised in steps of 5 degrees Celsius, waiting time was 10 minutes, the search detectivity was 0.02 degrees Celsius/minute, data output distance was 0.2 degrees Celsius, maximum measurement pressure was 170 bar in a nitrogen atmosphere. The initial exothermic temperature of the sample based on the ARC measurement data is shown Reference 2 of Table 3.

EXAMPLE 21-23

Heat Stabilization Examination by ARC Measurement on Diethylzinc

Similarly to Reference 2, carried out the examination of the diethylzinc composition to which was added aromatic compounds having an isopropenyl group as a side chain, which is a compound of the present invention. The initial exothermic temperature of the sample based on the ARC measurement data are shown in Example 21-23 of Table 4.

The initial exothermic temperature of the diethylzinc composition to which was added the aromatic compounds having an isopropenyl group as a side chain of the present invention is higher than the initial exothermic temperature of diethylzinc only. From this result, it is confirmed that the diethylzinc composition of the present invention has a superior heat stability.

TABLE 4

| Example | Diethylzinc composition | Additive | Ratio of the additive (%) | ARC sample quantity (g) | ARC initial exothermic temperature (° C.) |
|---|---|---|---|---|---|
| Example 21 | Diethylzinc-1,4-Diisopropenylbenzen | 1,4-Diisopropenylbenzen | 0.103 | 1.9305 | 160.18 |
| Example 22 | Diethylzinc-1,4-Diisopropenylbenzen | 1,4-Diisopropenylbenzen | 0.500 | 1.9120 | 170.25 |
| Example 23 | Diethylzinc-α-Methylstyrene | α-Methylstyrene | 0.478 | 1.9691 | 165.25 |
| Reference 2 | Diethylzinc | None | 0 | 1.9211 | 140.37 |

EXAMPLE 24-50 AND REFERENCE 3-11

Calculated TMR (Time to Maximum Rate) at each temperature concerning diethylzinc and various kinds of diethylzinc compositions based on ARC measurement data provided by embodiment 21-23 and reference 2. In the calculation of TMR, used the J. E. Huff method, that is, pursues a formula which extrapolates self exothermic speed and TMR to a cold side, calculate self exothermic speed and TMR provided after (Φ) amendment at each temperature.

Out of the ARC measurement range (less than 50 degrees Celsius), TMR is calculated using an approximate formula, this approximate formula is provided from the data of 4 points, that is data of 50 degrees Celsius, 60 degrees Celsius, 70 degrees Celsius, and 80 degrees Celsius.

A value of TMR of diethylzinc which does not have an additive assumed 1, and a value of TMR of the diethylzinc composition to which was added the aromatic compounds having an isopropenyl group as a side chain of the present invention is calculated as a relative value to the above mentioned value (1) in each temperature. That is, a relative value of TMR of the diethylzinc composition to which an additive was added is larger than 1, TMR (Time to Maximum Rate) becomes long and it shows superior heat stability in comparison with the diethylzinc composition which does not have an additive.

EXAMPLE 24-26 AND REFERENCE 3

A value of TMR of diethylzinc which does not have an additive (reference 3) at 120 degrees Celsius is assumed 1, the relative value of TMR (Time to Maximum Rate) of each diethylzinc composition are showed in Table 5. From the result of example 24.26 in Table 5, it is clearly demonstrates that the diethylzinc composition which was provided by adding an additive of the present invention has high heat stability since a relative value of (TMR) is greater than 1,

TABLE 5

| Example | Diethylzinc composition | Additive | Ratio of the additive (%) | Time of maximum exothermic speed (TMR) relative value* |
|---|---|---|---|---|
| Example 24 | Diethylzinc-1,4-Diisopropenylbenzen | 1,4-Diisopropenylbenzen | 0.103 | 1.9305 |
| Example 25 | Diethylzinc-1,4-Diisopropenylbenzen | 1,4-Diisopropenylbenzen | 0.500 | 1.9120 |
| Example 26 | Diethylzinc-α-Methylstyrene | α-Methylstyrene | 0.478 | 1.9691 |
| Reference 3 | Diethylzinc | None | 0 | 1.9211 |

*The relative value that calculated a value of (TMR) of diethylzinc without the additive for 1

EXAMPLE 27-29 AND REFERENCE 4

A value of TMR of diethylzinc which does not have an additive (reference 4) at 100 degrees Celsius is assumed 1, relative values of TMR (Time to Maximum Rate) of each diethylzinc composition are showed in Table 6. From the result of example 27-29 in Table 6, it is clearly demonstrated that the diethylzinc composition which was provided by adding an additive of the present invention has high heat stability since a relative value of (TMR.) is greater than 1,

TABLE 6

| Example | Diethylzinc composition | Additive | Ratio of the additive (%) | Time of maximum exothermic speed (TMR) relative value* |
|---|---|---|---|---|
| Example 27 | Diethylzinc-1,4-Diisopropenylbenzen | 1,4-Diisopropenylbenzen | 0.103 | 1.91 |

TABLE 6-continued

| Example | Diethylzinc composition | Additive | Ratio of the additive (%) | Time of maximum exothermic speed (TMR) relative value* |
|---|---|---|---|---|
| Example 28 | Diethylzinc-1,4-Diisopropenylbenzen | 1,4-Diisopropenylbenzen | 0.500 | 8.53 |
| Example 29 | Diethylzinc-α-Methylstyrene | α-Methylstyrene | 0.478 | 2.14 |
| Reference 4 | Diethylzinc | None | 0 | 1 |

*The relative value that calculated a value of (TMR) of diethylzinc without the additive for 1

EXAMPLE 30-32 AND REFERENCE 5

A value of TMR of diethylzinc which does not have an additive (reference 5) at 80 degrees Celsius is assumed 1, relative values of TMR (Time to Maximum Rate) of each diethylzinc composition are showed in Table 7. From the result of example 30-32 in Table 7, it is clearly demonstrated that the diethylzinc composition which was provided by adding an additive of the present invention has high heat stability since a relative value of (TMR) is greater than 1,

TABLE 7

| Example | Diethylzinc composition | Additive | Ratio of the additive (%) | Time of maximum exothermic speed (TMR) relative value* |
|---|---|---|---|---|
| Example 31 | Diethylzinc-1,4-Diisopropenylbenzen | 1,4-Diisopropenylbenzen | 0.103 | 2.33 |
| Example 32 | Diethylzinc-1,4-Diisopropenylbenzen | 1,4-Diisopropenylbenzen | 0.500 | 16.07 |
| Example 33 | Diethylzinc-α-Methylstyrene | α-Methylstyrene | 0.478 | 2.69 |
| Reference 5 | Diethylzinc | None | 0 | 1 |

*The relative value that calculated a value of (TMR) of diethylzinc without the additive for 1

EXAMPLE 33-35 AND REFERENCE 6

A value of TMR of diethylzinc which does not have an additive (reference 6) at 80 degrees Celsius is assumed 1, relative values of TMR (Time to Maximum Rate) of each diethylzinc composition are showed in Table 8. From the results of example 33-35 in Table 8, it is clearly demonstrated that the diethylzinc composition which was provided by adding an additive of the present invention has high heat stability since a relative value of (TMR) is greater than 1.

TABLE 8

| Example | Diethylzinc composition | Additive | Ratio of the additive (%) | Time of maximum exothermic speed (TMR) relative value* |
|---|---|---|---|---|
| Example 33 | Diethylzinc-1,4-Diisopropenylbenzen | 1,4-Diisopropenylbenzen | 0.103 | 2.91 |
| Example 34 | Diethylzinc-1,4-Diisopropenylbenzen | 1,4-Diisopropenylbenzen | 0.500 | 32.69 |
| Example 35 | Diethylzinc-α-Methylstyrene | α-Methylstyrene | 0.478 | 3.49 |
| Reference 6 | Diethylzinc | None | 0 | 1 |

*The relative value that calculated a value of (TMR) of diethylzinc without the additive for 1

EXAMPLE 36-38 AND REFERENCE 7

A value of TMR of diethylzinc which does not have an additive (reference 7) at 40 degrees Celsius is assumed 1, relative values of TMR (Time to Maximum Rate) of each diethylzinc composition are showed in Table 9. From the results of examples 36-38 in Table 9, it is clearly demonstrated that the diethylzinc composition which was provided by adding an additive of the present invention has high heat stability since a relative value of (TMR) is greater than 1,

TABLE 9

| Example | Diethylzinc composition | Additive | Ratio of the additive (%) | Time of maximum exothermic speed (TMR) relative value* |
|---|---|---|---|---|
| Example 36 | Diethylzinc-1,4-Diisopropenylbenzen | 1,4-Diisopropenylbenzen | 0.103 | 3.83 |
| Example 37 | Diethylzinc-1,4-Diisopropenylbenzen | 1,4-Diisopropenylbenzen | 0.500 | 68.81 |
| Example 38 | Diethylzinc-α-Methylstyrene | α-Methylstyrene | 0.478 | 4.91 |
| Reference 7 | Diethylzinc | None | 0 | 1 |

*The relative value that calculated a value of (TMR) of diethylzinc without the additive for 1

EXAMPLE 39-41 AND REFERENCE 8

A value of TMR of diethylzinc which does not have an additive (reference 8) at 30 degrees Celsius is assumed 1, relative values of TMR (Time to Maximum Rate) of each diethylzinc composition are showed in Table 10. From the result of examples 39-41 in Table 10, it is clearly demonstrated that the diethylzinc composition which was provided by adding an additive of the present invention has high heat stability since a relative value of (TMR) is greater than 1,

TABLE 10

| Example | Diethylzinc composition | Additive | Ratio of the additive (%) | Time of maximum exothermic speed (TMR) relative value* |
|---|---|---|---|---|
| Example 39 | Diethylzinc-1,4-Diisopropenylbenzen | 1,4-Diisopropenylbenzen | 0.103 | 4.74 |
| Example 40 | Diethylzinc-1,4-Diisopropenylbenzen | 1,4-Diisopropenylbenzen | 0.500 | 136.47 |
| Example 41 | Diethylzinc-α-Methylstyrene | α-Methylstyrene | 0.478 | 6.31 |
| Reference 8 | Diethylzinc | None | 0 | 1 |

*The relative value that calculated a value of (TMR) of diethylzinc without the additive for 1

EXAMPLE 42-44 AND REFERENCE 9

A value of TMR of diethylzinc which does not have an additive (reference 9) at 25 degrees Celsius is assumed 1, relative values of TMR (Time to Maximum Rate) of each diethylzinc composition are showed in Table 11. From the result of examples 42-44 in Table 11, it is clearly demonstrated that the diethylzinc composition which was provided by adding an additive of the present invention has high heat stability since a relative value of (TMR) is greater than 1,

TABLE 11

| Example | Diethylzinc composition | Additive | Ratio of the additive (%) | Time of maximum exothermic speed (TMR) relative value* |
|---|---|---|---|---|
| Example 42 | Diethylzinc-1,4-Diisopropenylbenzen | 1,4-Diisopropenylbenzen | 0.103 | 5.42 |
| Example 43 | Diethylzinc-1,4-Diisopropenylbenzen | 1,4-Diisopropenylbenzen | 0.500 | 210.61 |
| Example 44 | Diethylzinc-α-Methylstyrene | α-Methylstyrene | 0.478 | 7.36 |
| Reference 9 | Diethylzinc | None | 0 | 1 |

*The relative value that calculated a value of (TMR) of diethylzinc without the additive for 1

EXAMPLE 45-47 AND REFERENCE 10

A value of TMR of diethylzinc which does not have an additive (reference 10) at 20 degrees Celsius is assumed 1, relative values of TMR (Time to Maximum Rate) of each diethylzinc composition are showed in Table 12. From the result of examples 45-47 in Table 12, it is clearly demonstrated that the diethylzinc composition which was provided by adding an additive of the present invention has high heat stability since a relative value of (TMR) is greater than 1,

TABLE 12

| Example | Diethylzinc composition | Additive | Ratio of the additive (%) | Time of maximum exothermic speed (TMR) relative value* |
|---|---|---|---|---|
| Example 45 | Diethylzinc-1,4-Diisopropenylbenzen | 1,4-Diisopropenylbenzen | 0.103 | 6.40 |
| Example 46 | Diethylzinc-1,4-Diisopropenylbenzen | 1,4-Diisopropenylbenzen | 0.500 | 358.2 |
| Example 47 | Diethylzinc-α-Methylstyrene | α-Methylstyrene | 0.478 | 8.90 |
| Reference 10 | Diethylzinc | None | 0 | 1 |

*The relative value that calculated a value of (TMR) of diethylzinc without the additive for 1

EXAMPLE 48-50 AND REFERENCE 11

A value of TMR of diethylzinc which does not have an additive (reference 11) at 10 degrees Celsius is assumed 1, relative values of TMR (Time to Maximum Rate) of each diethylzinc composition are showed in Table 13. From the result of examples 48-50 in Table 13, it is clearly demonstrated that the diethylzinc composition which was provided by adding an additive of the present invention has high heat stability since a relative value of (TMR) is greater than 1.

TABLE 13

| Example | Diethylzinc composition | Additive | Ratio of the additive (%) | Time of maximum exothermic speed (TMR) relative value* |
|---|---|---|---|---|
| Example 48 | Diethylzinc-1,4-Diisopropenylbenzen | 1,4-Diisopropenylbenzen | 0.103 | 10.68 |
| Example 49 | Diethylzinc-1,4-Diisopropenylbenzen | 1,4-Diisopropenylbenzen | 0.500 | 1864.58 |
| Example 50 | Diethylzinc-α-Methylstyrene | α-Methylstyrene | 0.478 | 16.04 |
| Reference 11 | Diethylzinc | None | 0 | 1 |

*The relative value that calculated a value of (MR) of diethylzinc without the additive for 1

EXAMPLE 51-52 AND REFERENCE 12

Long-term Heat Stability Examination

Prepared a sample of the diethylzinc composition by the method that is defined in the paragraph on the preparation of the diethylzinc composition, put the sample into the 200 mL withstand pressure autoclave comprising a glass interpolation container, and carried out an acceleration examination of heated and stored at 70 degrees Celsius for 32 days. Similarly examination was carried out on the diethylzinc composition which did not have an additive using a 200 mL withstand pressure autoclave (reference 12). After the examination, opened the autoclave under a nitrogen atmosphere, and, for each sample, confirmed a deposition state of the deposit by viewing. And, under a nitrogen atmosphere, removed diethylzinc and washed a deposit with hexane and dried the remaining deposit. It was confirmed that the remaining deposit was zinc metal by ICP analysis. When precipitated zinc was retrievable, assayed by weighting, and when the quantity of precipitated zinc was too small to be retrievable, washed container with 10% nitric acid water solution, and assayed an absolute quantity of zinc in nitric acid solution.

The quantity of the deposit which generated by thermolysis of diethylzinc which does not have an additive assumed 1, and the quantity of the deposit generated by the thermolysis of the diethylzinc composition to which was added an additive is calculated as a relative value to the above mentioned value 1. That is, a relative value of the quantity of deposit of the diethylzinc composition to which was added an additive is smaller than 1, it shows superior heat stability in comparison with diethylzinc composition which does not add an additive.

Relative value of precipitated zinc of each samples are shown in Table 14. From example 51-52 in Table 14, the quantity of the deposit which generated by the thermolysis of the diethylzinc composition which added an additive was less than $1/50^{th}$ of the quantity of the deposit which generated by thermolysis of diethylzinc which did not add an additive, then, it is ensured that the diethylzinc composition which was provided by adding an additive of the present invention has high heat stability for a long time.

TABLE 14

| Example | Diethylzinc composition | Additive | Ratio of the additive (%) | Zinc precipitation quantity (relative value)* |
|---|---|---|---|---|
| Reference 4 | Diethylzinc | None | 0 | 1 |
| Example 51 | Diethylzinc-1,4-Diisopropenylbenzen | 1,4-Diisopropenylbenzen | 0.103 | <0.02 |
| Example 52 | Diethylzinc-1,4-Diisopropenylbenzen | 1,4-Diisopropenyibenzen | 0.500 | <0.02 |

*Relative value calculated a value diethylzinc without the additive for 1

EXAMPLE 53-55 AND REFERENCE 12-14

Example 53-55

As an aromatic compounds of the present invention having isopropenyl as a side chain, prepared a sample shown in Table 15, a additive which improves heat stability of diethylzinc and hexane which is different types of hydrocarbons with the additive and toluene which is an aromatic hydrocarbon compound were coexisted in the sample. Similarly to Example 1-5, carried out the examination of thermal analysis to the samples, the initial exothermic temperature of each sample are shown in Table 15 in conformity.

REFERENCE 12-14

Prepared samples in Table 15, these samples are similarly to Example 53-55 except not adding 1, 3-diisopropenyl benzene of the present invention. Similarly to Example 1-5, carried out the examination of thermal analysis to the samples, the initial exothermic temperature of each sample are shown in Table 15 in conformity.

From result of example 53-55 and reference 12-14, it is ensured that the aromatic compounds of the present invention having isopropenyl as a side chain is effective as the additive which improved heat stability of diethylzinc, even if hexane which is different types of hydrocarbons with the additive and toluene which is an aromatic hydrocarbon compound were coexisted.

EXAMPLE 56-62

Heat Stabilization Examination by DSC Measurement to Diethylzinc

Similarly to Reference 1, under a nitrogen atmosphere, weighted a diethylzinc composition which added 1) particular aromatic compounds having isopropyl group bonded to a side chain, 2) particular compound having fulvene structure, 3) squalene, 4) 2,4-diphenyl-4-methyl-1-pentene as a liquid compound at temperature of 25 degrees Celsius, and sealed in a DSC cell made of SUS. Similarly to Reference 1, carried out a thermal analysis on the provided sample by the DSC method, the measurement temperature range was 30-450 degrees Celsius, and the rise speed of temperature was 10 degrees Celsius/minute. The initial exothermic temperature of the samples are shown in Table 16.

The initial exothermic temperature of the sample of the diethylzinc composition which added various kinds of the aromatic compounds of the present invention is higher than the initial exothermic temperature of the sample of diethylzinc only provided by the reference, and the start temperature of the resolution of the composition of the present invention is higher than the start temperature of the sample of diethylzinc only. From this result, it is confirmed that the diethylzinc composition which was added to an additive has a superior heat stability.

TABLE 15

| Example | Diethylzinc composition | Additive | Ratio of the additive (%) | DSC sample quantity (mg) | DSC initial exothermic temperature (° C.) |
|---|---|---|---|---|---|
| Example 53 | 67.3 weight % Diethylzinc-1,3-Diisopropenylbenzen-Hexane | 1,3-Diisopropenylbenzen | 3.6 | 2.1 | 191.4 |
| Example 54 | 48.5 weight % Diethylzinc-1,3-Diisopropenylbenzen-Toluene | 1,3-Diisopropenylbenzen | 4.0 | 2.3 | 204.3 |
| Example 55 | 67.7 weight % Diethylzinc-1,3-Diisopropenyibenzen-Toluene | 1,3-Diisopropenylbenzen | 3.7 | 2.5 | 202.5 |
| Comparative Example 12 | 69.8 weight % Diethylzinc-Hexane | None | 0 | 2.1 | 170.4 |
| Comparative Example 13 | 50.3 weight % Diethylzinc-Toluene | None | 0 | 2.2 | 187.2 |
| Comparative Example 14 | 70.2 weight % Diethyizinc-Toluene | None | 0 | 2.4 | 177.3 |

Also, the additives are liquid at 25 degrees Celsius, then a preparation of diethylzinc composition can be performed easily.

COMPARATIVE EXAMPLE 15-21

Similarly to example 56-62, as an aromatic compounds which have not a isopropyl group as a side chain, prepare benzene and toluene which replaced the isopropyl of compound of example 56-62 with hydrogen. And carried out a similar examination to the diethylzinc composition which added benzene and toluene. The initial exothermic temperatures of the samples are shown in Table 16.

From result of comparative example 15-21, it is confirmed that the samples are inferior to a composition of the present invention which is added an aromatic compounds having a isopropyl group as a side chain in heat stability, and from this result it is confirmed that it is high effect in heat stability if isopropyl is bonded as a side chain.

COMPARATIVE EXAMPLE 22-24

Similarly to Example 56-62, carried out the examination to the diethylzinc composition which was added anthracene, acenaphthene and acenaphthylene, these are the compounds as described in Prior art 1-3. The initial exothermic temperatures of the samples are shown in Table 16.

Among these samples, the initial exothermic temperature of anthracene and acenaphthene are lower than the initial exothermic temperature of the sample of the diethylzinc composition which is added additives of the present invention, and the composition which added an existing additive is inferior to the composition of the present invention in heat stability. The thermostable effect of the diethylzinc composition which added acenaphthylene is slightly higher than the additive of the present invention, however, these well-known compound have 25 degrees Celsius or more melting point, then those are solid at the general handling temperature (25 degrees Celsius), when mix them to diethylzinc with ignition characteristics in the aim, complicated equipment such as the solid injection machines that maintained nitrogen atmosphere requires. On the other hand, the additive of the present invention is a liquid at room temperature, therefor, if it provides a tank and the injection line where substitution is easy for nitrogen atmosphere, the additive can be added to diethylzinc.

TABLE 16

| Example | Diethylzinc composition | Additive | Ratio of the additive (%) | DSC sample quantity (mg) | DSC initial exothermic temperature (° C.) | Property of the additive (25° C.) | Melting temperature of the additive (° C.) |
| --- | --- | --- | --- | --- | --- | --- | --- |
| Reference 1 | Diethylzinc | None | 0 | 2.7 | 182.9 | None | None |
| Example 56 | Diethylzinc-6,6-Dimethylfulvene | 6,6-Dimethylfulvene | 3.89 | 2.9 | 207.5 | Liquid | 3 |
| Example 57 | Diethylzinc-1,4-Diisopropilbenzen | 1,4-Diisopropilbenzen | 3.30 | 2.6 | 192.6 | Liquid | −17 |
| Example 58 | Diethylzinc-1,3-Diisopropilbenzen | 1,3-Diisopropilbenzen | 3.78 | 3.1 | 190.4 | Liquid | −63 |
| Example 59 | Diethylzinc-1,3,5-Triisopropyl benzene | 1,3,5-Triisopropylbenzene | 3.83 | 2.9 | 195.6 | Liquid | −7 |
| Example 60 | Diethylzinc-2-Isopropilnaphthalene | 2-Isopropilnaphthalene | 3.85 | 2.6 | 198.3 | Liquid | 14 |
| Example 61 | Diethylzinc-Squalene | Squalene | 3.86 | 2.8 | 194.2 | Liquid | −75 |
| Example 62 | Diethylzinc-2,4-Diphenyl-4-Methyl-1-Pentene | 2,4-Diphenyl-4-Methyl-1-Pentene | 3.96 | 2.9 | 197.0 | Liquid | −82 |
| Comparative Example 15 | Diethylzinc-Benzene | Benzene | 3.96 | 2.8 | 177.0 | Liquid | 6 |
| Comparative Example 16 | Diethylzinc-Toluene | Toluene | 3.77 | 2.9 | 178.7 | Liquid | −25 |
| Comparative Example 17 | Diethylzinc-1,7-Dimethylnaphthalene | 1,7-Dimethylnaphthalene | 3.73 | 2.9 | 186.0 | Liquid | 22~24 |
| Comparative Example 18 | Diethylzinc-1,3,5-Trimethylbenzene | 1,3,5-Trimethylbenzene | 3.97 | 2.9 | 178.9 | Liquid | −45 |
| Comparative Example 19 | Diethylzinc-Cumene | Cumene | 3.84 | 2.9 | 183.2 | Liquid | −96 |
| Comparative Example 20 | Diethylzine-1,3,5-Tri-tert-butylbenzene | 1,3,5-Tri-tert-butylbenzene | 3.39 | 2.9 | 177.1 | Liquid | 69~71 |
| Comparative Example 21 | Diethylzinc-2,6-Di-tert-butylnaphtalene | 2,6-Di-tert-butyl-naphtalene | 3.88 | 2.8 | 183.9 | Solid | 148 |
| Comparative Example 22 | Diethylzinc-Anthracene | Anthracene | 4.36 | 3.3 | 188.7 | Solid | 216 |
| Comparative Example 23 | Diethylzinc-Acenaphthylene | Acenaphthylene | 4.43 | 3.4 | 173.5 | Solid | 93 |
| Comparative Example 24 | Diethylzinc-Acenaphthene | Acenaphthene | 4.27 | 1.8 | 201.9 | Solid | 90~95 |

EXAMPLE 63

Similarly to example 56-62, carried out a thermal analysis to example 63 changing addition rate, the initial exothermic temperatures of the samples are shown in Table 17.

TABLE 17

| Example | Diethylzine composition | Additive | Ratio of the additive (%) | DSC sample quantity (mg) | DSC initial exothermic temperature (° C.) |
| --- | --- | --- | --- | --- | --- |
| Example 63 | Diethylzinc-6,6-Dimethylfulvene | 6,6-Dimethylfulvene | 0.49 | 2.7 | 195.8 |

Even if it changes the addition rate of the additives, the initial exothermic temperature of the sample of the diethylzinc composition which was added a compound of the present invention is higher than the initial exothermic temperature of the sample of diethylzinc only provided by the reference, also the start temperature of the resolution of the sample of the present invention is higher than the sample of diethylzinc only.

From this result, it is confirmed that the diethylzinc composition which was added to an additive has a superior heat stability.

COMPARATIVE EXAMPLE 25-27

Similarly to Example 56-60, carried out the thermal analysis to the diethylzinc composition which was added anthracene, acenaphthene and acenaphthylene changing addition rate, the initial exothermic temperatures of the samples are shown in Table 18. When an addition rate of the additive was low, heat stability of the composition which added an existing additive was inferior to a composition of the present invention.

TABLE 18

| Example | Diethylzinc composition | Additive | Ratio of the additive (%) | DSC sample quantity (mg) | DSC initial exothermic temperature (° C.) |
| --- | --- | --- | --- | --- | --- |
| Comparative Example 25 | Diethylzinc-Anthracene | Anthracene | 0.48 | 2.7 | 187.0 |
| Comparative Example 26 | Diethylzinc-Acenaphthylene | Acenaphthylene | 0.49 | 2.8 | 171.9 |
| Comparative Example 27 | Diethylzinc-Acenaphthene | Acenaphthene | 0.50 | 2.7 | 175.9 |

EXAMPLE 64-68

Heat Stabilization Examination by DSC Measurement to Diethylzinc Composition

Similarly to Reference 1, under a nitrogen atmosphere, weighted naphthalene, 2-methylnaphthalene, 2,6-diisopropyl naphthalene, 1-styryl naphthalene and 2-methoxynaphthalene as the naphthalene compound which is with 85 degrees Celsius or less of melting point or freezing point, and sealed in a DSC cell made of SUS. Similarly to Reference 1, carried out a thermal analysis to the provided samples by DSC method, the measurement temperature range was 30-450 degrees Celsius, and the rise speed of temperature was 10 degrees Celsius/minute. The initial exothermic temperature of the samples are shown in Table 19.

The initial exothermic temperature of the sample of the diethylzinc composition which added various kinds of additives of the present invention is higher than the initial exothermic temperature of the sample of diethylzinc only provided by the reference, and the start temperature of the resolution of the composition of the present invention is higher than the start temperature of the sample of diethylzinc only. From this result, it is confirmed that the diethylzinc composition which was added to an additive has a superior heat stability.

Melting points of each additive are as follows;
Naphthalene: 80 degrees Celsius
2-methyl naphthalene: 31 degrees Celsius
2,6-diisopropyl naphthalene: 70 degrees Celsius
1-styryl naphthalene: 70 degrees Celsius
2-methoxynaphthalene: 73 degrees Celsius
Both are lower than the melting point of the well-known additive.

COMPARATIVE EXAMPLE 28-30

Similarly to Example 64-68, carried out the thermal analysis to the diethylzinc composition which was added anthracene, acenaphthene and acenaphthylene these are the compounds as described in Prior art 1-3. the initial exothermic temperatures of the samples are shown in Table 19.

Among these samples, the initial exothermic temperature of anthracene and acenaphthene are lower than the initial exothermic temperature of the sample of the diethylzinc composition which is added additives of the present invention, the composition which added an existing additive is inferior to a composition of the present invention in heat stability. The thermostable effect of the diethylzinc composition which added acenaphthylene is slightly higher than the additive of the present invention, however, The melting point of these well-known compound are higher than the additive of the present invention. that is, anthracene: 216 degrees Celsius, acenaphthene: 93 degrees Celsius, acenaphthylene: 90-95 degrees Celsius.

TABLE 19

| Example | Diethylzinc composition | Additive | Ratio of the additive (%) | DSC sample quantity (mg) | DSC initial exothermic temperature (° C.) | Melting temperature of the additive (° C.) |
|---|---|---|---|---|---|---|
| Reference 1 | Diethylzinc | None | 0 | 2.7 | 182.9 | None |
| Example 64 | Diethylzinc-2-Methylnaphthalene | 2-Methylnaphthalene | 3.89 | 2.8 | 199.5 | 31 |
| Example 65 | Diethylzinc-2-Methoxynaphthalene | 2-Methoxynaphthalene | 3.93 | 2.8 | 200.1 | 73 |
| Example 66 | Diethylzinc-1-Styrylnaphthalene | 1-Styrylnaphthalene | 3.90 | 2.8 | 193.3 | 70 |
| Example 67 | Diethylzinc-2,6-Diisopropylnaphthalene | 2,6-Diisopropylnaphthalene | 3.43 | 2.9 | 193.2 | 70 |
| Example 68 | Diethylzinc-Naphthalene | Naphthalene | 4.03 | 2.7 | 192.4 | 80 |
| Comparative Example 28 | Diethylzinc-Anthracene | Anthracene | 4.36 | 3.3 | 188.7 | 216 |
| Comparative Example 29 | Diethylzinc-Acenaphthylene | Acenaphthylene | 4.43 | 3.4 | 173.5 | 93 |
| Comparative Example 30 | Diethylzinc-Acenaphthene | Acenaphthene | 4.27 | 1.8 | 201.9 | 90~95 |

EXAMPLE 69-70

Heat Stabilization Examination by DSC Measurement to Diethylzinc Composition Similarly to Reference 1, under a nitrogen atmosphere, weighted a diethylzinc composition which is added a compound having azulene structure, and sealed in a DSC cell made of SUS. Similarly to Reference 1, carried out a thermal analysis to the provided samples by DSC method, the measurement temperature range was 30-450 degrees Celsius, and the rise speed of temperature was 10 degrees Celsius/minute. The initial exothermic temperature of the samples are shown in Table 20.

The initial exothermic temperature of the sample of the diethylzinc composition which added a compound having azulene structure is higher than the initial exothermic temperature of the sample of diethylzinc only provided by the reference, and the start temperature of the resolution of the composition of the present invention is higher than the start temperature of the sample of diethylzinc only. From this result, it is confirmed that the diethylzinc composition which was added to an additive has a superior heat stability.

COMPARATIVE EXAMPLE 31-33

Similarly to Example 69-70, carried out the examination to the diethylzinc composition which was added anthracene, acenaphthene and acenaphthylene, these are the compounds as described in Prior art 1-3. The initial exothermic temperatures of the samples are shown in Table 20.

The initial exothermic temperature of these samples are lower than the initial exothermic temperature of the sample added a compound having azulene structure of the present invention, the composition which added an existing additive is inferior to a composition of the present invention in heat stability.

TABLE 20

| Example | Diethylzinc composition | Additive | Ratio of the additive (%) | DSC sample quantity (mg) | DSC initial exothermic temperature (° C.) |
|---|---|---|---|---|---|
| Reference 1 | Diethylzinc | None | 0 | 2.7 | 182.9 |
| Example 69 | Diethylzinc-Azulene | Azulene | 0.39 | 2.6 | 202.4 |
| Example 70 | Diethylzinc-Guaiazulene | Guaiazulene | 0.40 | 3.0 | 200.5 |
| Comparative Example 31 | Diethylzinc-Anthracene | Anthracene | 0.48 | 2.7 | 187.0 |
| Comparative Example 32 | Diethylzinc-Acenaphthene | Acenaphthene | 0.49 | 2.8 | 171.9 |
| Comparative Example 33 | Diethylzinc-Acenaphthene | Acenaphthene | 0.50 | 2.7 | 175.9 |

The invention claimed is:
1. A heat stabilization method, comprising
selecting, as an additive in a diethylzinc composition, an aromatic compound having an isopropenyl group as a side chain,
wherein the additive is selected from the group consisting of formula (1), (2) and (3):

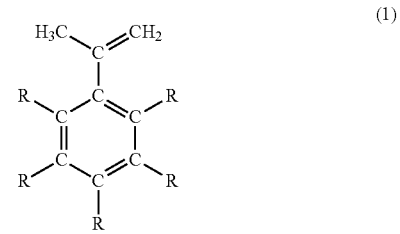

-continued

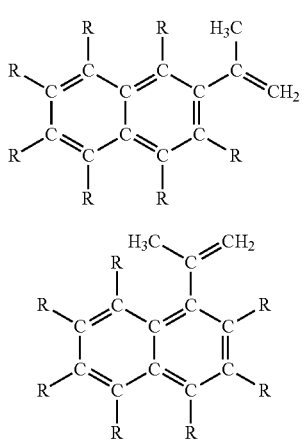

(2)

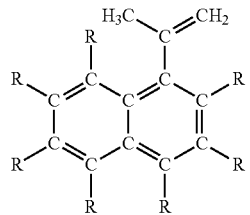

(3)

wherein in formula (1), (2) and (3), R represents respectively, hydrogen, a straight chain or branched alkyl group which has 1-8 carbon atoms, a straight chain or branched alkenyl group, including an isopropenyl group, which has 1-8 carbon atoms, an allyl group which has 6-14 carbon atoms, and wherein in formula (1), at least one R group is not hydrogen; and adding the additive to the diethylzinc at a ratio of 100 ppm to 20 wt %.

2. The heat stabilization method according to claim 1, further comprising:

adding a saturated, an unsaturated or a mixture of saturated and unsaturated hydrocarbon having 5-25 carbon atoms.

* * * * *